United States Patent [19]
Messerschmidt et al.

[11] Patent Number: 5,636,633
[45] Date of Patent: Jun. 10, 1997

[54] DIFFUSE REFLECTANCE MONITORING APPARATUS

[75] Inventors: Robert G. Messerschmidt; Mark R. Robinson, both of Albuquerque, N.M.

[73] Assignee: Rio Grande Medical Technologies, Inc., Albuquerque, N.M.

[21] Appl. No.: 513,094

[22] Filed: Aug. 9, 1995

[51] Int. Cl.[6] .............................. A61B 5/00; G01N 21/47
[52] U.S. Cl. ......................... 128/633; 128/664; 356/446; 250/341.8
[58] Field of Search ...................... 356/446; 250/339.11, 250/341.8; 128/633, 664

[56] References Cited

U.S. PATENT DOCUMENTS

| | | | |
|---|---|---|---|
| 3,508,830 | 4/1970 | Hopkins et al. | 250/339.11 |
| 4,655,225 | 4/1987 | Dahne et al. | 128/633 |
| 4,661,706 | 4/1987 | Messerschmidt et al. | 250/341 |
| 4,852,955 | 8/1989 | Doyle et al. | 350/1.2 |
| 4,853,542 | 8/1989 | Milosevic et al. | 356/446 |
| 4,975,581 | 12/1990 | Robinson et al. | 250/339 |
| 5,015,100 | 5/1991 | Doyle | 356/445 |
| 5,019,715 | 5/1991 | Sting et al. | 250/571 |
| 5,051,602 | 9/1991 | Sting et al. | 250/571 |
| 5,355,880 | 10/1994 | Thomas et al. | 128/633 |
| 5,379,764 | 1/1995 | Barnes et al. | 128/633 |
| 5,452,723 | 9/1995 | Wu et al. | 128/664 |
| 5,533,509 | 7/1996 | Koashi et al. | 128/633 |

OTHER PUBLICATIONS

Marbach, "Measurement Techniques for IR Spectroscopic Blood Glucose Determination", 1993.
Doyle and McIntosh, Paper No. 24, 16th Annual FACSS Conference, Oct., 1989.

*Primary Examiner*—Angela D. Sykes
*Assistant Examiner*—Eric F. Winakur
*Attorney, Agent, or Firm*—Nawrocki, Rooney & Sivertson, P.A.

[57] ABSTRACT

An improved apparatus for diffuse reflectance spectroscopy having a specular control device. The specular control device has at least a first surface divided into an even-numbered plurality of reflecting sections and open or transmitting sections. The number of reflecting sections is equal to the number of open sections. Each reflecting section is situated between a pair of open sections and opposite to another reflecting section. Similarly, each open section is situated between a pair of reflecting sections and is opposite to another open section. In one preferred embodiment, the total surface area of the reflecting sections is equal to the total surface area of the open sections. In another embodiment, the total surface area of the reflecting sections is unequal to the total surface area of the open sections. In another preferred embodiment, opaque spacers are provided on the borders between adjacent sections to improve the detecting definition between source and reflected beams, and, to selectively provide for decreasing surface area of one or more selected sections.

14 Claims, 9 Drawing Sheets

DIFFUSE REFLECTANCE MONITORING APPARATUS

TECHNICAL FIELD

The present invention relates generally to diffuse reflectance spectroscopy; and more particularly, to an improved apparatus for the spectroscopic measurement or analysis of an analyte concentration in human tissue; and, still more particularly, to an improved apparatus including a specular reflectance control device for use in such a measurement system.

BACKGROUND OF THE INVENTION

The need and demand for an accurate, non-invasive method for determining analyte concentrations in human tissue is well documented. Barnes et al. (U.S. Pat. No. 5,379,764), for example, disclose the necessity for diabetics to frequently monitor glucose levels in their blood. It is further recognized that the more frequent the analysis, the less likely there will be large swings in glucose levels. These large swings are associated with syptoms and complications of the disease, whose long term effects can include heart disease, arteriosclerosis, blindness, stroke, hypertension, kidney failure, and premature death. As described below, systems have been proposed for the non-invasive measurement of glucose in blood. However, despite these efforts, a lancet cut into the finger is still necessary for all presently commercially available forms of home glucose monitoring. This is believed so compromising to the diabetic patient that the most effective use of any form of diabetic management is rarely achieved.

The various proposed non-invasive methods for determining blood glucose level, discussed individually below, generally utilize quantitative infrared spectroscopy as a theoretical basis for analysis. Infrared spectroscopy measures the electromagnetic radiation (0.7–25 µm) a substance absorbs at various wavelengths. Atoms do not maintain fixed positions with respect to each other, but vibrate back and forth about an average distance. Absorption of light at the appropriate energy causes the atoms to become excited to a higher vibration level. The excitation of the atoms to an excited state occurs only at certain discrete energy levels, which are characteristic for that particular molecule. The most primary vibrational states occur in the mid-infrared frequency region (i.e., 2.5–25 µm). However, non-invasive analyte determination in blood in this region is problematic, if not impossible, due to the absorption of the light by water. The problem is overcome through the use of shorter wavelengths of light which are not as attenuated by water. Overtones of the primary vibrational states exist at shorter wavelengths and enable quantitative determinations at these wavelengths.

It is known that glucose absorbs at multiple frequencies in both the mid- and near-infrared range. There are, however, other infrared active analytes in the blood which also absorb at similar frequencies. Due to the overlapping nature of these absorption bands, no single or specific frequency can be used for reliable non-invasive glucose measurement. Analysis of spectral data for glucose measurement thus requires evaluation of many spectral intensities over a wide spectral range to achieve the sensitivity, precision, accuracy, and reliability necessary for quantitative determination. In addition to overlapping absorption bands, measurement of glucose is further complicated by the fact that glucose is a minor component by weight in blood, and that the resulting spectral data may exhibit a non-linear response due to both the properties of the substance being examined and/or inherent non-linearities in optical instrumentation.

Robinson et al. (U.S. Pat. No. 4,975,581) disclose a method and apparatus for measuring a characteristic of unknown value in a biological sample using infrared spectroscopy in conjunction with a multivariate model that is empirically derived from a set of spectra of biological samples of known characteristic values. The above-mentioned characteristic is generally the concentration of an analyte, such as glucose, but also may be any chemical or physical property of the sample. The method of Robinson et al. involves a two-step process that includes both calibration and prediction steps. In the calibration step, the infrared light is coupled to calibration samples of known characteristic values so that there is differential attenuation of at least several wavelengths of the infrared radiation as a function of the various components and analyte comprising the sample with known characteristic value. The infrared light is coupled to the sample by passing the light through the sample or by reflecting the light from the sample. Absorption of the infrared light by the sample causes intensity variations of the light that are a function of the wavelength of the light. The resulting intensity variations at the at least several wavelengths are measured for the set of calibration samples of known characteristic values. Original or transformed intensity variations are then empirically related to the known characteristic of the calibration samples using a multivariate algorithm to obtain a multivariate calibration model. In the prediction step, the infrared light is coupled to a sample of unknown characteristic value, and the calibration model is applied to the original or transformed intensity variations of the appropriate wavelengths of light measured from this unknown sample. The result of the prediction step is the estimated value of the characteristic of the unknown sample. The disclosure of Robinson et al. is incorporated herein by reference.

Dähne et al. (U.S. Pat. No. 4,655,225) further disclose a method utilizing near infrared spectroscopy for non-invasively transmitting optical energy in the near infrared spectrum through a finger or earlobe of a subject. Dähne also disclose measuring reflected light energy to determine analyte concentration. The reflected light energy is further stated as comprised of light reflected from the surface of the sample and light reflected from deep within the tissue. It is the near infrared energy diffusely reflected from deep within the tissues that Dähne disclose as containing analyte information, while surface reflected light energy gives no analyte information and interferes with interpreting or measuring light reflected from deep in the tissue. The present invention is directed to an apparatus for improved measurement of diffusely reflected light, while eliminating the effects of surface reflected light.

Reflectance spectroscopy is known in other non-medical applications. In general, such spectroscopy is concerned with identification of the chemical structure of the sample through the use of reflected information. Diffuse reflectance spectroscopy is also generally known, and is widely used in the visible and near-infrared regions of the light spectrum to study materials such as grains and other food products.

In broad terms, diffuse reflectance spectroscopy utilizes the fact that the sample materials will tend to scatter light in a more or less random fashion. A fraction of the light will eventually be scattered back from the sample and collected by a detector to provide a quantitative or qualitative representation of the sample.

In infrared spectroscopy it is often desirable to use the mid-infrared region of the spectrum. The fundamental vibrational absorptions described earlier are strongest here, in the fundamental region. The goal of infrared spectroscopy sampling is often to prepare a sample so that it may be analyzed with this mid-infrared light. Reflectance spectroscopy is one very popular way of making a sample compatible with mid-infrared light. If a sample is too thick to get any light through in transmission, often a result can be obtained by reflectance. Reflectance spectroscopy is complicated however, by the fact that there is more than one optical phenomenon occurring in this mode. Reflectance of light from a sample can be largely divided into two categories, diffuse reflectance and specular reflectance. The specular reflectance of a sample is the light which does not generate into the sample, but rather reflects "like a mirror" from the front surface of the sample. This component contains information about the sample at the surface. If the material is homogeneous, this surface reflection can be related to the bulk. While the specular component does not physically appear much like an absorbance spectrum, it can be related to the absorbance spectrum of the bulk material through a transformation called the Kramers-Kronig transformation. Still, most experts agree that the diffuse component is much more useful for sample qualifications and quantification than is the specular component. There has been a lot of effort, by the applicants and by others, to enhance the diffuse component, and de-emphasize the specular component and to essentially cause the reflectance spectrum to be more transmission-like. Generally these efforts fall largely into three categories: optical discrimination against specular, mechanical discrimination, and secondary methods of sample preparation designed to minimize specular. A fourth, non-independent approach is to move away from the mid-infrared region in order to relax the sample preparation requirements. By moving to the near-infrared or visible region of the spectrum, the vibrational spectroscopy becomes more blunt and imprecise, but often this can be made up for by the improvements observed in the quality and signal-to-noise ratio of the data obtained because of improved sampling ability, more appropriate path length, and better discrimination against specular reflectance. This approach is especially useful when quantitative information is desired.

Most experts would agree that the diffuse component is desirable, and even essential, if the sample material is layered or non-homogeneous. The specular component will largely contain information about the surface of the sample and not about the bulk. Nevertheless, U.S. Pat. No. 5,015,100, issued May 14, 1991 to Walter M. Doyle, describes an example of the specular approach. The specular component of the light is significantly wavelength dependent, and contains information about the complex refractive index of the material under test. This complex refractive index contains an imaginary term which relates to the absorption coefficient of the material.

Doyle indicates that the potential utility of specular reflectance spectroscopy is well-known to those of skill in the art and points out that mathematical expressions, namely the Kramers-Kronig relation, can be used to convert measured reflectance spectra into absorbance spectra. These calculated spectra are then useful for identifying samples by comparison with existing libraries of absorbance spectra. However, the work of the prior art has not been used for quantitative measurements such as the composition analysis of samples such as a patient's blood. In fact, it would perform poorly for this purpose, since there is little blood information at the surface of the skin. The diffuse component must be used.

Paper No. 424, presented at the 16th Annual FACSS Conference in October, 1989, by Doyle and Mcintosh, concluded that the Kramers-Kronig relations could not be used to obtain accurate absorbance spectra from reflectance data unless the equations used were modified to take into consideration polarization and angle of incidence, or unless the experimental apparatus provided radiation which approximated the conditions at normal incidence.

The Doyle patent reference describes the use of apparatus in a specular reflectance system in which the analytical radiation reflected by the sample approximates the conditions existing at normal incidence, and proposed a solution by ensuring essentially equal contributions from rays polarized parallel to the plane of incidence and from rays polarized perpendicular to the plane of incidence. Doyle teaches that a semi-transparent beamsplitter used in such an apparatus would achieve the desired polarization balance, but would sacrifice radiation efficiency because of losses in pre-sample transmission, post-sample reflection, and absorbance loss in the beamsplitter. The Doyle reference then described a system of improved radiation efficiency utilizing a split field beamsplitter having a surface area divided into an uneven plurality of reflecting blades and open transmitting areas.

U.S. Pat. No. 4,852,955 also issued to Doyle, describes a system which obviates the problem of limited beamsplitter efficiency by using a 100% reflecting mirror intercepting half of the system aperture, and arranging for the illuminating and outgoing beams to use opposite halves of the aperture. However, the use of the split field beamsplitter of this reference involves a distribution of incident radiation which is asymmetrical with respect to an axis normal to the sample surface. As a result, there is no assurance that the p and s polarization states will be balanced when the suggested beamsplitter is in use.

The limitations of Doyle's prior art are clear. Specular reflectance is only useful when the bulk material is adequately represented by surface composition. When this is not the case, such as when performing non-invasive blood analyte measurements, this methodology will give a spurious result.

An example of a mechanical discrimination against specular reflectance is shown in U.S. Pat. No. 4,661,706, issued Apr. 28, 1987, to Robert G. Messerschmidt and Donald W. Sting. Messerschmidt et al. demonstrate that the specular and the diffuse component of reflected light can be separated mechanically, taking advantage of the fact that the specular component emanates from the surface of the sample. A blade-like device "skims" the specular light before it can impinge on the detector. Pure diffuse reflectance can be obtained after a careful alignment. A disadvantage of the device is that it is not very efficient in collecting the diffuse light. Much diffusely reflected energy travels only a shallow depth into the specimen, and it is at this boundary that the blocker device resides. The shallow depth diffuse light is therefore excluded. For very highly absorbing samples in the mid-infrared region, the signal-to-noise ratio of the resultant measurement is strongly compromised. This type of device could be used successfully for non-invasive blood analyte measurements, but with reduced efficiency compared with the method proposed in this application.

Optical means have also been used to separate diffuse and specular components. A recent example is described by Ralf Marbach in his PhD. thesis entitled "MeBverfahren zur IRspektroskopishen Blutglucose bestimmung" (English translation: "Measurement Techniques for IR Spectroscopic Blood Glucose Determination"), and published in Duesseldorf in 1993. Marbach employs an optical discrimination system quite similar in principle to that used by Harrick Scientific Corp. in the Praying Mantis diffuse reflectance instrument first introduced in 1980. The concept here is that the specular light reflects from a sample with an angle equal and opposite to the angle of incidence to the surface normal. Using this fact, it is a simple matter to collect light only outside the input collection angle. Marbach and Harrick then limit the input angle to a small range, so that a larger range of output angles may be used for collection. Note that there is a limited region of space over which light can be launched into and collected from a sample. In terms of solid angle, for a planar surface sample, this working volume can be stated to be $2\pi$ steradians in solid angle. In the Harrick device, a small and equal solid angle is subtended by the input and the output optics. Less than $\frac{1}{2}\pi$ steradians is subtended by either the input or the output optic. This leads to an efficiency of less than 50% of the available solid angle. Another critical factor in collecting diffusely reflected light is the directionality of the collected light. Many samples, including the tissue samples required for non-invasive measurements are quite forward scattering. That is to say that a scattered photon will change only a small angle in direction after a scattering event. The Harrick device requires a photon to deviate through a large angle before it can be collected by the output optics. This poor performance in the presence of sample anisotropy and the relatively low efficiency are severe problems with the Harrick device. The Marbach device improves on the Harrick device in a number of ways. First, the total volume available for input and collection of light approaches $2\pi$ steradians which is the theoretical limit. This is accomplished by allowing 360° azimuthal angular subtense for both the input and output light. Second, the forward directionality of scatter is taken into account. Rays which deviate only a few degrees in angle can be collected. The downfall of this approach is that the input and output optical systems are completely unmatched in terms of magnification. Any diffuse reflectance system must work in concert with the source and the detector of the system. Since detectors in the near-infrared region of the spectrum get noisier when they get bigger, it should be a goal to make the detector as small as possible. A bright compact source is also advantageous. In the Marbach system, the image of the source is very much magnified relative to the image of the detector in the sample plane. This means that the source energy density which can be imaged onto the detector is limited. In addition, the collected energy from the sample is demagnified as it travels to the detector. Again, energy efficiency is compromised. An ideal situation would leave the input and output magnifications equal. Another important limitation of the Marbach design relates to the choice of angles for input and output. Real optical systems are good at imaging with large f/numbers. Small f/number systems, especially with large field stop diameters, tend to image poorly. Marbach notes this fact in his thesis. In his design, the prime, large f/number, near-normal space is all reserved for input light, and the non-ideal near-grazing light is used for output. It is quite conceivable that the device would work better if used "backwards" from the mode employed by Marbach, where the source site and the detector site would be switched. The device described in this application provides an even better solution.

Another method of eliminating specular contribution to a diffuse reflectance spectrum is to modify the sample itself to reduce its propensity to reflect specularly. One way to accomplish this is to dilute a powdered sample in a non-absorbing matrix material with a low refractive index. The low index matrix will have a low amount of specular component and will mitigate the specular problem. Unfortunately, the goal of non-invasive analysis does not allow for modification of the sample, and so in the field of use described here, these dilution methods are not an option.

SUMMARY OF THE INVENTION

The apparatus of the present invention is a device for improved measurement of diffusely reflected light from analyte containing human tissue. The apparatus incorporates a specular control device which separates the specularly reflected light or surface reflected light from the diffusely reflected light returning from deep within the tissue. Therefore, only the diffusely reflected light containing analyte information reaches the spectroscopic analyzer. The improved specular control device of the present invention includes a surface intended to be incident to the analytical beam from a light source, which surface is divided into an even numbered plurality of sections, half of the sections being clear for passing light beams, and half of the sections comprising reflecting mirrors for directing reflected beams from the sample to detection apparatus.

Applicants have found that the use of a specular control device based on symmetrical distribution of the input and output optics can reduce or eliminate specular light contamination associated with diffuse reflectance sampling of human tissue.

In a preferred embodiment, the light rays from an energy source are focused onto a tissue sample by an optical system, preferably composed of lenses. The light passes through or is incident upon the specular control device described in further detail below. It has been found that focusing the beam causes any light entering the system and undergoing specular reflectance to exit the system on the opposite side of the focus center. Specifically, light rays undergoing specular reflection will travel a path which is symmetric about the center focus. Thus, specularly reflected light will travel a path that has center point symmetry. The specular control device, the optical system is symmetric about the center focus. For example, light which is specularly reflected off the surface of the skin will exit the optical system on the opposite side of the beam focus, which corresponds to an opposing opening in the specular control device. Non-specularly reflected light which has undergone a change in direction relative to its angle of incidence to the center focus will be incident on the surface of the specular control device in a non-windowed portion and will be diverted for subsequent spectral analysis. Thus, specularly reflected light never reaches the analyzer.

In a first preferred embodiment of the specular control device, there are a minimum of four sections, half of which are open, and half of which are reflecting. Each reflecting section is situated between a pair of open sections and is opposite to another reflecting section about the center point of the specular control device. In this preferred embodiment, the total surface area of the reflecting sections is substantially equal to the total surface area of the open sections of the specular control device.

In a second preferred embodiment of the specular control device, which is a variation of the above-described embodiment, an opaque space of predetermined width serves as a border between each adjacent section. The opaque space may be placed along centerlines of the surface such that the total surface area of the reflecting sections is equal to the total surface area of the open sections; or the opaque space can be selectively placed off-center in a manner such that the total surface area of the reflecting sections is unequal to the total surface area of the open sections.

BRIEF DESCRIPTION OF THE DRAWINGS

Other objects and many of the attendant advantages of the present invention will be readily appreciated as they become better understood by reference to the following detailed description when considered in connection with the accompanying drawings, in which drawings like reference numerals designate like parts throughout the figures thereof and wherein.

DETAILED DESCRIPTION OF THE PREFERRED EMBODIMENTS

The present invention is directed to an improved apparatus for spectrographic analysis or measurement of an analyte concentration. In preferred embodiments, the apparatus is utilized for measuring analyte concentrations in tissue of human patients, more particularly, the invention is focused on analyzing glucose concentration in the tissue. The basis for measurement is diffusely reflected light returning from the tissue sample after being illuminated by a wide-band near-infrared energy source.

Figure 1:
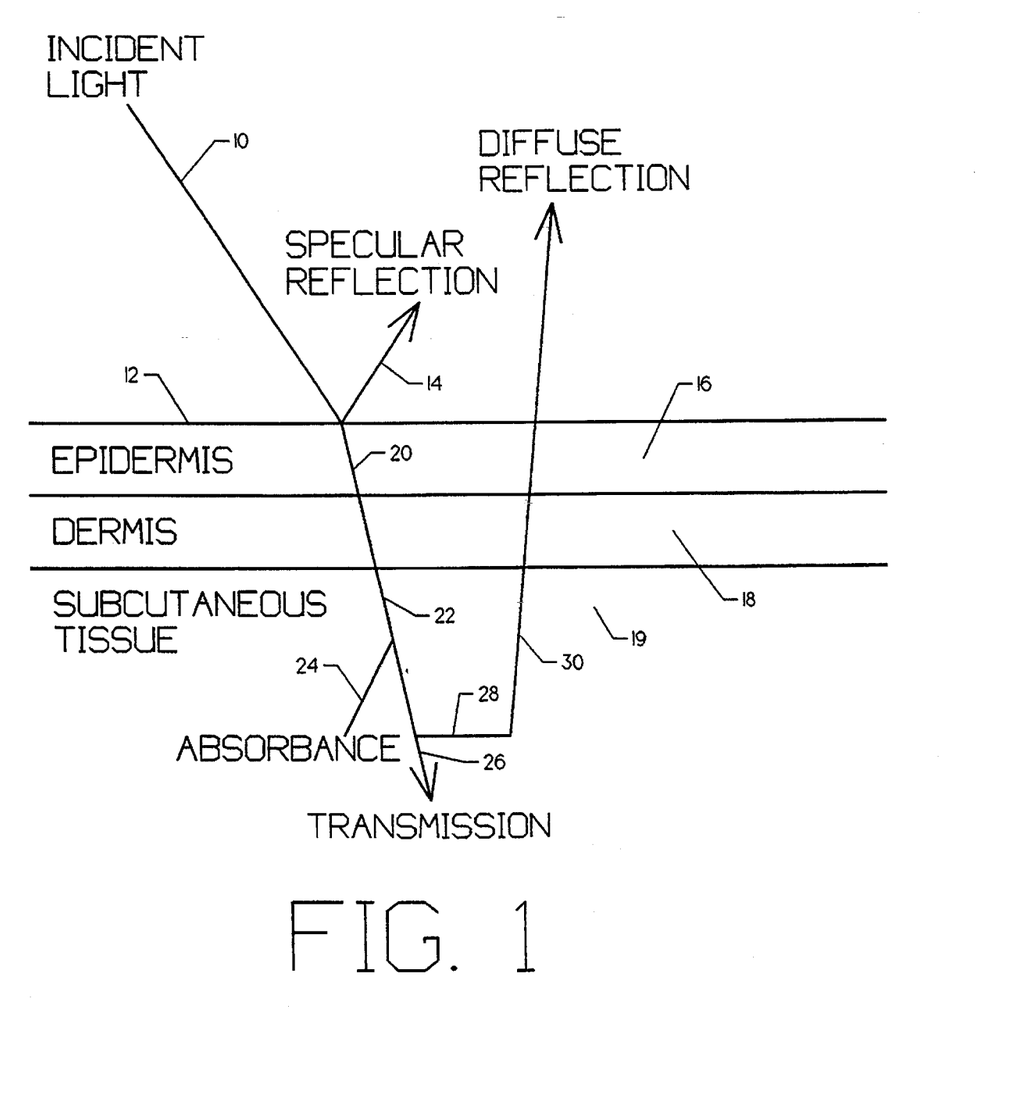
FIG. 1 is a simplified schematic showing the alternative responses to light incident on an analyte-containing tissue, including specular reflection, diffuse reflection, absorption and transmission.

Referring first to FIG. 1, a schematic representation of light energy incident on an analyte-containing tissue sample is depicted. As depicted in the simplified representation, a tissue sample 12 includes an upper layer or epidermis 16, a middle layer or dermis 18 and subcutaneous tissue 19. Incident light 10 illuminates the tissue sample 12, wherein portions of the light energy may be transmitted through the tissue sample, resulting in transmitted light 26 exiting the opposing side of the tissue sample. Alternatively, a tissue sample may absorb a portion of the light energy, resulting in absorbed light energy 24 as heat. A third phenomena includes specular reflection 14 of a portion of the incident light 10. Finally, a portion of the light energy can be diffusely reflected 30.

The diffusely reflected light 30 undergoes several refractions due to contact with the various components within the tissue sample. Eventually a portion of the diffusely reflected light energy 30 returns to the surface of the tissue sample 12 and exits back through the skin surface to the measuring device. Thus, both specular reflected light 14 and diffuse reflected light 30 combine and are directed back toward the instrument of the present invention.

Of the reflected light, only the diffusely reflected light 30 contains analyte or glucose information. The light, which is specularly reflected, contains information on the avascular epidermis, but does not contain glucose information. Thus, the goal of the present invention is to utilize only the diffusely reflected light 30 for analysis by separating such light from the specularly reflected light 14. Specularly reflected light 14 can be viewed as contamination light as it does not contain the necessary information for analysis.

Applicants have found that the problems associated with diffuse reflectance sampling of tissue can be minimized by the distribution of the input and output optics based on center symmetry. In a center symmetry configuration, the light rays 10 are focused onto the tissue sample 12 by an optical system, incorporating lenses. It has been found with this embodiment, the light rays which are specularly reflected off the surface of the tissue 12 exit the optical system on the opposite side of the beam focus. Any light ray entering the system and undergoing specular reflectance exits the system on the opposite side of the center focus.

Figure 2:
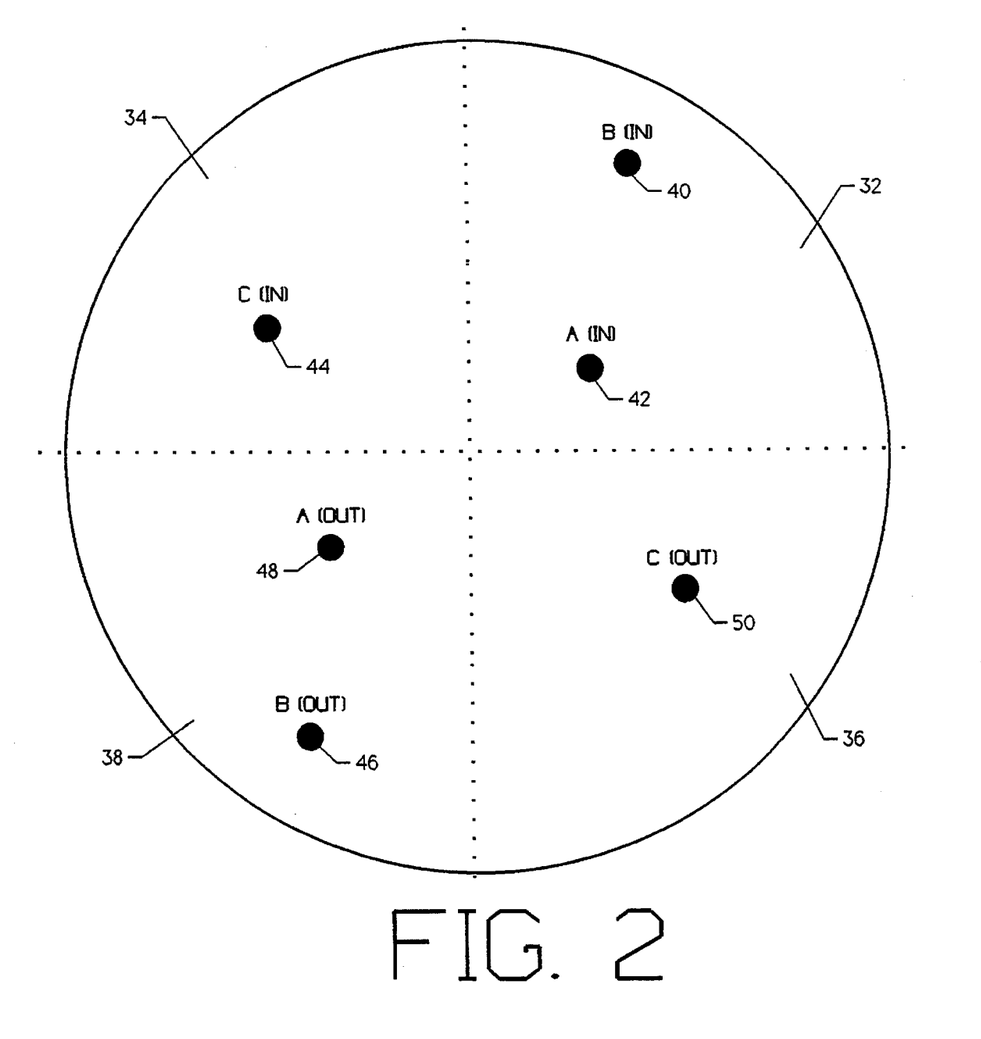
FIG. 2 is a schematic representation of the effect on spectral reflectance utilizing input and output rays symmetric about a center focus.

Referring now to FIG. 2, a schematic diagram is presented which illustrates the concept and effect on light rays passing through the lens system, which focuses the beam. As depicted in FIG. 2, light rays A, B, and C are depicted as passing through a generally circular transparent plate divided into four quadrants about the center point. The quadrants include first quadrant 32, second quadrant 34, third quadrant 38 and fourth quadrant 36. As represented, input light energy A 42 is incident on and passes through the plate in the first quadrant. Due to center point symmetry, the output light energy A 48 due to specular reflectance returns through the plate in the third quadrant. Likewise, input light energy B 40 is also incident on the first quadrant 32. Output light energy B 46, which is the result of spectral reflectance exits the third quadrant 38. Similarly, input light energy C 44, which is incident on the second quadrant 34, has a component of specularly reflected light which exits from the fourth quadrant 36 as indicated as output light energy C 50.

Figure 3:
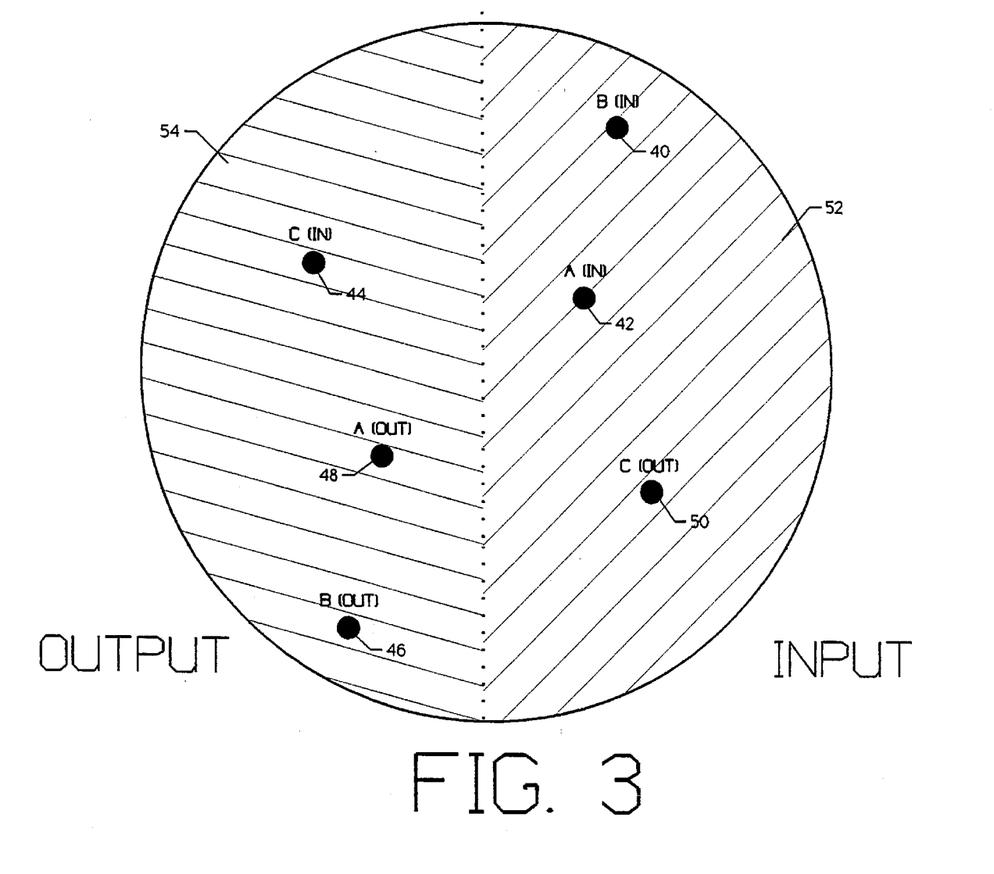
FIG. 3 depicts a typical single mirror optical configuration for reflectance sampling, wherein the optical beam is divided into an input and output side about a single center line.

In contrast to the concept of center point symmetry, a typical single mirror optical configuration for reflectance sampling includes an optical beamdivided into an input and an output side about a single center line. This configuration is depicted in FIG. 3. Again, a generally circular plate having an input side 52 and an output side 54 is depicted. The sides are divided by a center line passing through the diameter of the plate. Input rays A 42, B 40 and C 50, which pass through the plate, have specularly reflected components or output light energy A 48, B 46 and C 44, which are actually sampled by the output optics and will be seen by any detector.

Applicants have found that the problems associated with specular reflectance can be eliminated by designing a specular control device incorporating the concepts of center point symmetry as depicted in FIG. 1 to overcome the problems with standard single mirror optical configurations for reflectance sampling. Now referring to FIG. 4, a generally circular plate divided into four quadrants is depicted. With the configuration of FIG. 4, the first quadrant 32 and third quadrant 38 are defined as input quadrants. The second quadrant 34 and fourth quadrant 36 are defined as output quadrants. With this embodiment, the light energy source is incident on the circular plate. However, the input quadrants allow the light energy to pass through, while the output quadrants are opaque. Thus, only light incident on the input quadrants passes through the specular control device to contact the tissue sample.

Figure 4:
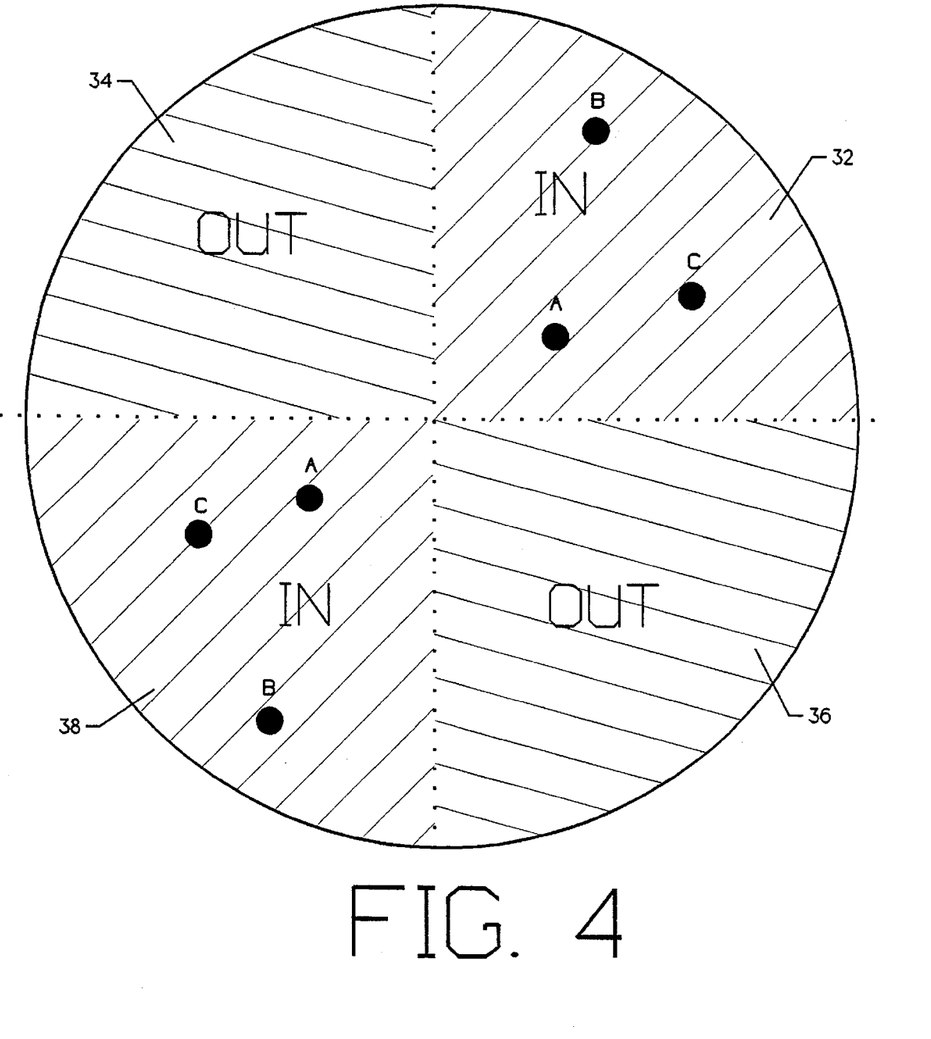
FIG. 4 is a schematic representation of the elimination of specularly reflected light utilizing four quadrants.

Light reflected from the tissue sample, including both specularly reflected light and diffusely reflected light is incident upon the opposite side of the specular control device. However, as explained for FIG. 1, all of the specularly reflected light returning from the tissue sample will be incident upon the first or third quadrants 32, 38 and will pass back through these openings. In contrast, a quantity of diffusely reflected light will be incident upon the second quadrant 34 and fourth quadrant 36 without any interfering specular reflection. The diffusely reflected light can then be reflected from the surface of the second and fourth quadrants 34, 36 and directed to the analyzer. In this way only the diffusely reflected light is analyzed.

Figure 5:
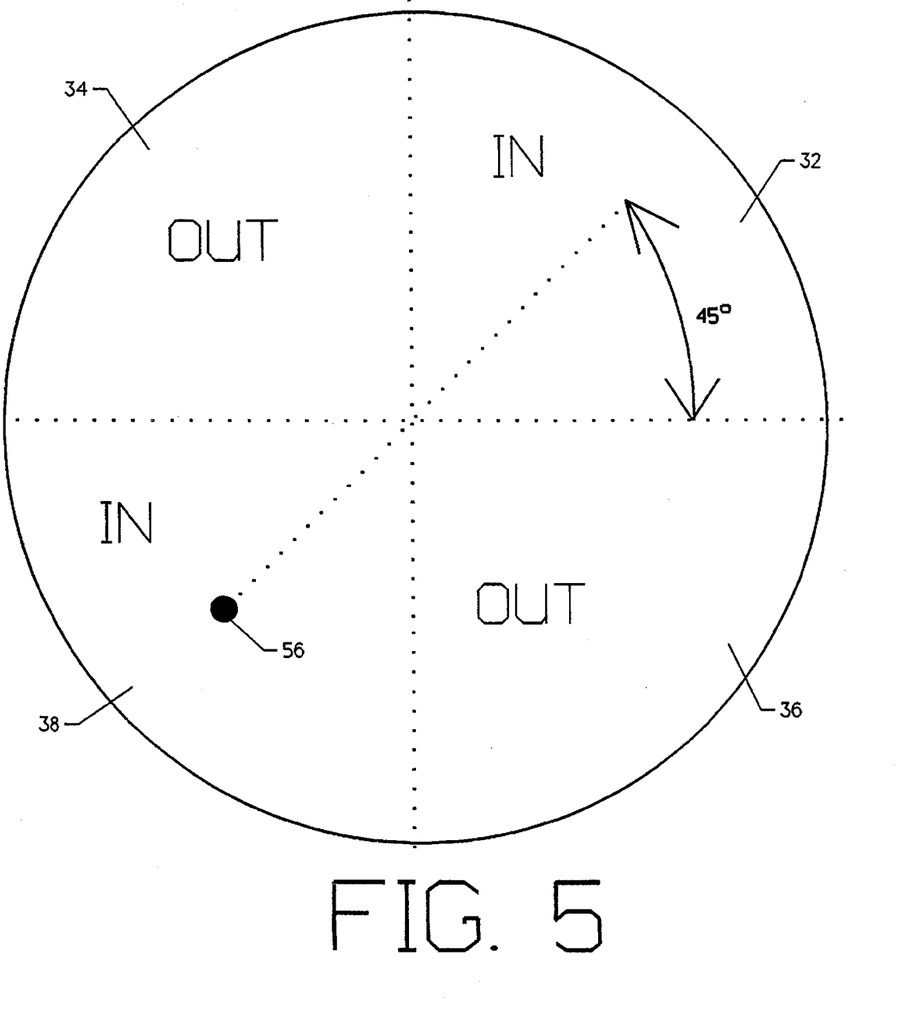
FIG. 5 is a schematic representation of directional change required for diffuse reflected light energy to reach the analyzer.
Figure 6:
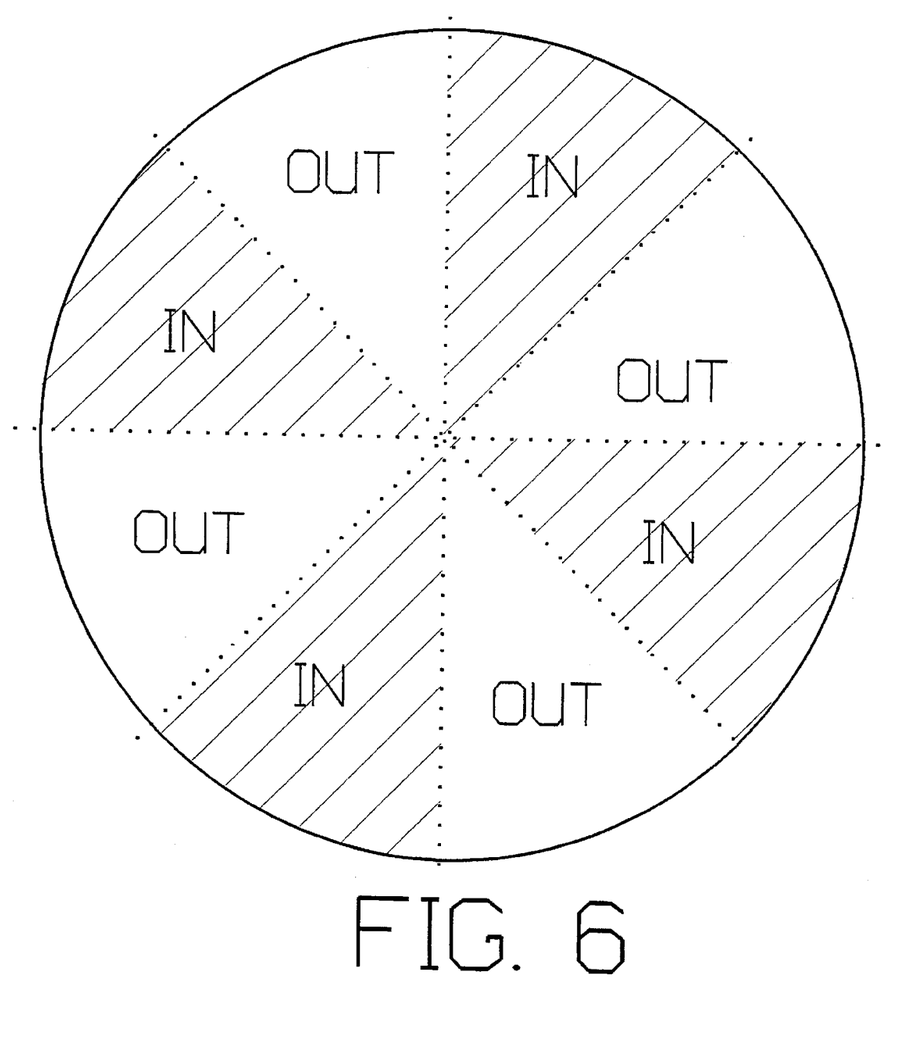
FIG. 6 is a schematic representation of a specular control device incorporating eight quadrants.
Figure 7:
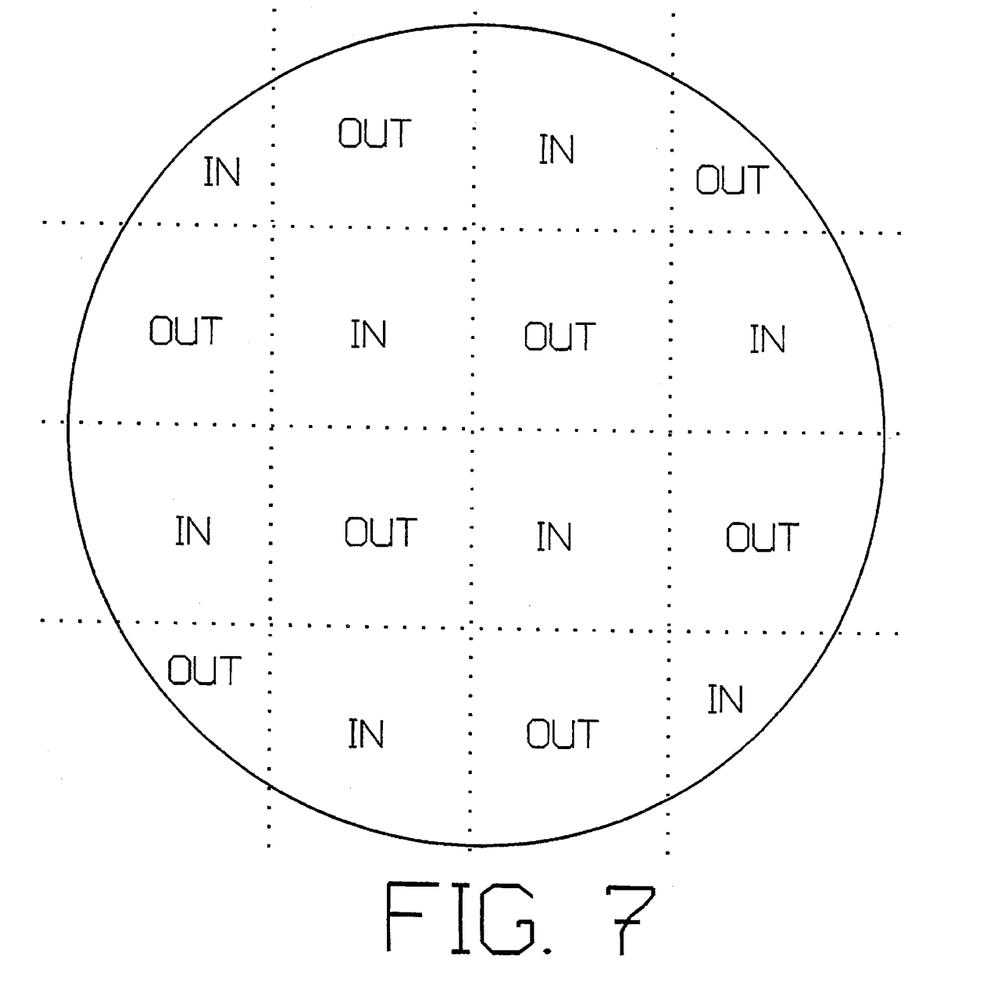
FIG. 7 is a schematic diagram of an alternative specular control device utilizing generally rectangular symmetric quadrants.

As shown in FIG. 5, the diffusely reflected portion of a light ray 56 would have to undergo a change in direction of at least 45 degrees before it could be collected by the output optics. It is recognized that the number of photons which would successfully complete this directional change without absorbance will be less than those that can successfully undergo a smaller directional change. Applicants have recognized that the efficiency of the optical system could be improved by further dividing the optical beam into numerous symmetrically based input and output sections. One such alternative embodiment is depicted in FIG. 6. In FIG. 6, the optical beam is divided into eight separate wedge shaped quadrants about the center point. In the eight quadrant configuration, a light ray located in the center of an input quadrant would have to undergo a directional change of only 22.5 degrees. Applicants recognize that the number of quadrants can be further increased. Alternatively, as depicted in FIG. 7, the optical beam can be divided into 16 generally square quadrants which are also symmetrical about the center point.

Figure 8A:
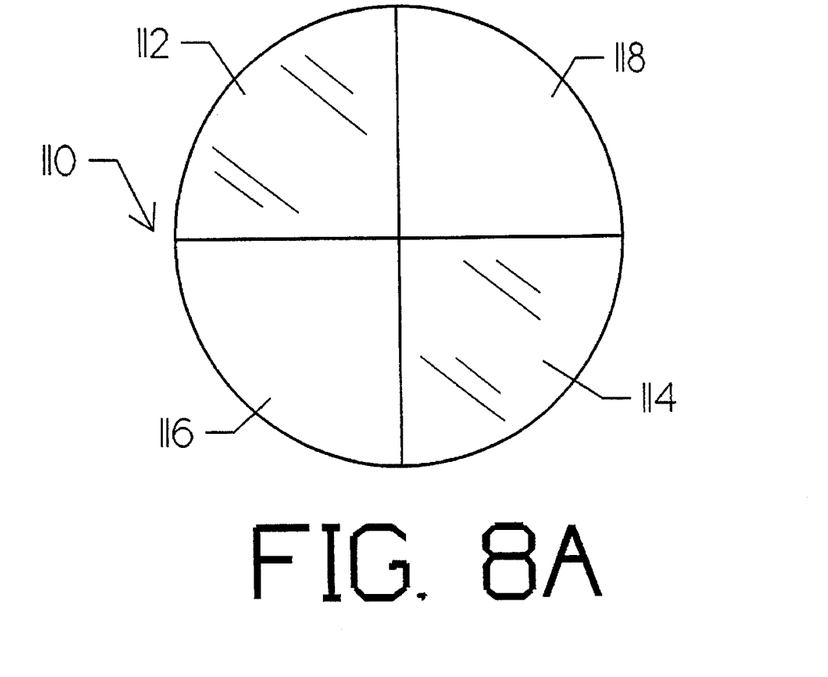
FIG. 8A is a plan view showing a first embodiment of the specular control device.

FIG. 8A discloses a specular control device indicated generally at 110. The surface of specular control device 110 is divided into an even numbered plurality of sections, here shown as open sections 116 and 118, and reflective sections 112 and 114. Open sections 116 and 118 are intended to pass or transmit any beam of light which is incident to the surface of specular control device 110.

In contrast, reflecting sections 112 and 114 are intended to block the incident beam and reflect portions of it to a predetermined site.

In the embodiment of FIG. 8A, each of sections 112, 114, 116 and 118 are of equal size and thus the total surface area of the open sections 116 and 118 is equal to the total surface area of reflecting sections 112 and 114. Further, each of reflecting sections 112 and 114 is situated between a pair of open sections 116 and 118; and, similarly, each of open sections 116 and 118 is located between a pair of reflecting sections 112 and 114. Finally, each reflecting section such as 112 is opposite to another reflecting section such as 114; and, each open section such as 116 is opposite to another open section such as 118.

Figure 8B:
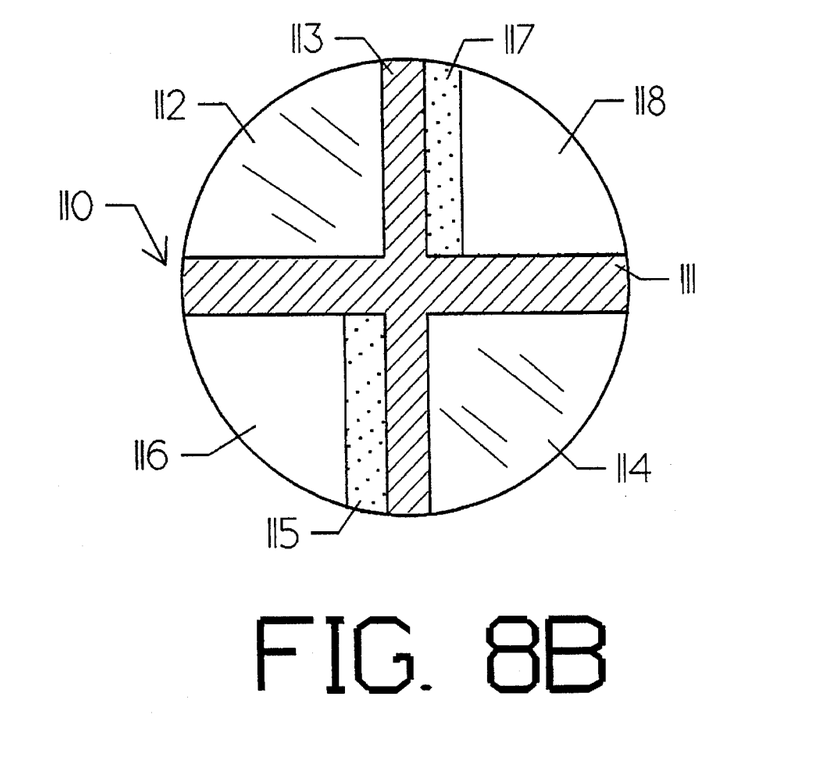
FIG. 8B is a plan view of a second embodiment of the specular control device.

Referring now to FIG. 8B, there is shown another embodiment of the apparatus of FIG. 8A. In FIG. 8B, specular control device 110 is again divided into a plurality of reflecting sections 112 and 114, and open sections 116 and 118. Each reflecting section such as 112 and 114 is situated between a pair of open sections 116 and 118, and similarly each of open sections 116 and 118 is situated between a pair of reflecting sections such as 112 and 114. Each reflecting section is opposite to another reflecting section, and each open section is opposite to another open section.

In FIG. 8B, there is also shown a set of opaque spacers 113 and 111 located along the borders between each of sections 112, 116, 114 and 118. The effect of spacers 111 and 113 is to achieve a more precise definition between the analytical beam sent to illuminate a sample and the data beam reflected from the sample. The opaque spacing between the reflecting and open sections achieves this desired improvement by, for example, preventing cross talk in the various adjacent sections from transmitted and reflected light beams.

When opaque spacers 111 and 113 are utilized along the diameters of a circular specular control device surface such as 110, they result in equal division of the remaining surface area between reflecting sections 112 and 114 and open sections 116 and 118. As it may be desirable for the analysis of certain samples to have the reflecting sections surface area unequal to the open sections surface area, this is shown accomplished in FIG. 8B by the addition of opaque spacers 115 and 117. For purposes of description, opaque area 115 has been shown as added to opaque spacer 113 to decrease the surface area of open section 116; and, similarly, opaque area 117 has been added to opaque spacer 113 to decrease the surface area of open section 118.

In the embodiment shown in FIG. 8B, in a system where the source analytical beam is transmitted through open areas 116 and 118, and the diffuse reflection from a sample is reflected by sections 112 and 114 to a detector, it will be apparent that the addition of opaque sections 115 and 117 will decrease the percentage of the source beam which illuminates the sample.

Figure 9:
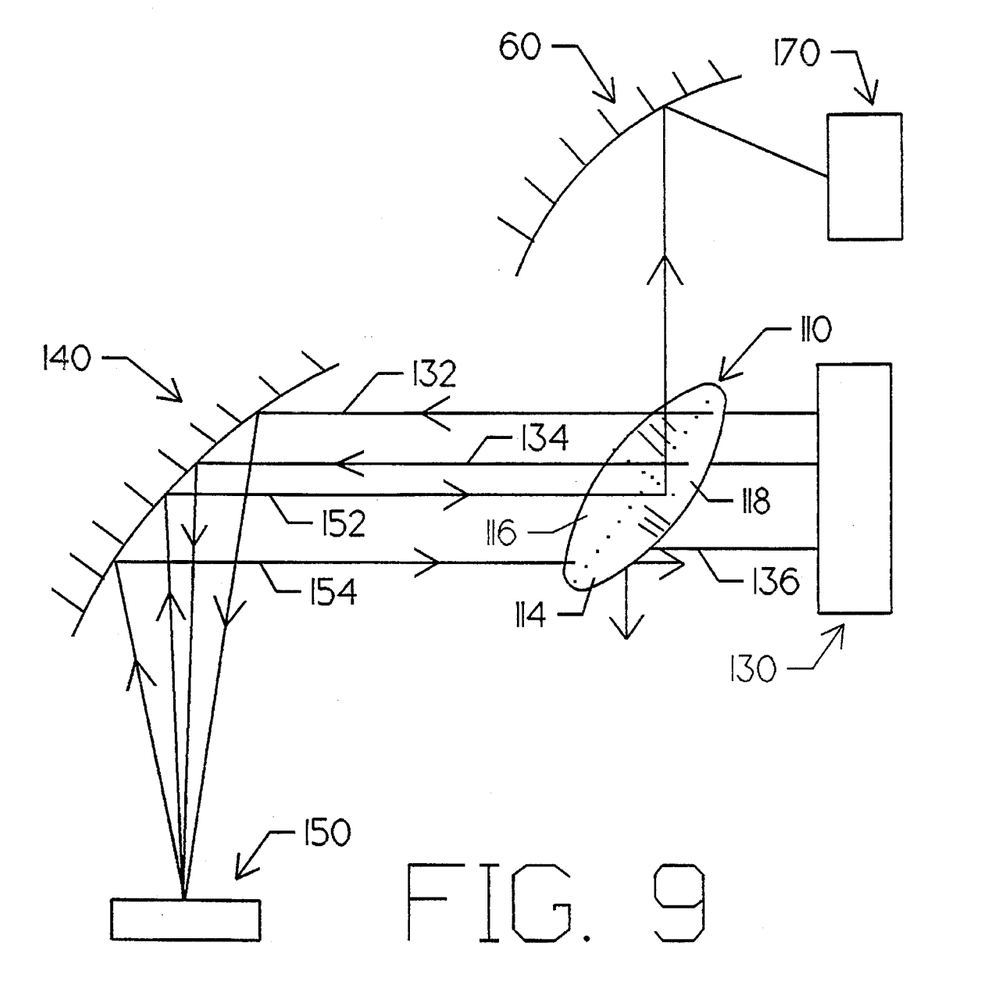
FIG. 9 is a schematic drawing showing the use of the specular control device of this invention in a spectroscopy system.

Referring now to FIG. 9, there is shown a schematic of a diffuse reflectance spectroscopy system utilizing the apparatus of this invention. A specular control device 110 is shown having open area 118 and reflective area 114. It is recognized that specular control device 110 need not be of a circular configuration as shown in FIGS. 8A and 8B but could be, for example, elliptical or rectangular in shape.

A light or energy source 130 is shown for providing an analytical source beam indicated at 132, 134 and 136. Source beam 132, 134 and 136 impinges on a first surface of specular control device 110. That portion of the source beam indicated at 136 is incident to reflecting portion 114 of specular control device 110 and is reflected away as shown by the arrow. That portion of the source beam indicated at 132 and 134 passes through open area 118 of specular control device 110, and continues on to be reflected by an elliptical mirror 140 to a desired focus on sample 150.

A diffuse reflectance beam 152 is reflected from sample 150 to mirror 140 and thence to the reflective surface 114 as shown by the arrows. Diffusely reflected beam 152 is reflected onto an elliptical mirror 60 from which it is focused into a detector 170 where the beam is analyzed.

In contrast to the diffusely reflected beam 152, a specularly reflected beam of light 154 is represented in FIG. 9. As is shown in FIG. 9, the specularly reflected beam 154 is reflected from the sample 150 to the mirror 140. This specularly reflected beam then passes through the open area 116 which is the open quadrant opposing the input quadrant 118 through which that light beam entered. The specularly reflected light 154 is thus not reflected to the analyzer 170 as described above for the diffusely reflected beam 152.

In FIG. 9, specular control device 110 could be a single element of the type generally known and having the reflective and open sections as shown in FIGS. 8A and 8B. Or, should it be desirable for manufacturing purposes, specular control device 110 could be a unit of a desired thickness having a first and second surface, each of which surface is treated in the same manner shown in FIGS. 8A and 8B. The reflecting and open sections on a first surface would be directly opposite the reflecting and open surfaces on a second surface to achieve the desired results.

Having thus described the preferred embodiments of the present invention, those of skill in the art will readily appreciate the other useful embodiments within the scope of the claims hereto attached.

What is claimed is:

1. An apparatus for obtaining a diffuse reflectance spectra from human tissue for the non-invasive measurement of blood analytes comprising;
   (a) means for generating infrared energy;
   (b) means for directing said infrared energy to said tissue;
   (c) means for collecting infrared energy that is reflected by said tissue; and
   (d) means for separating said reflected light to obtain infrared energy that has been diffusely reflected from said tissue, said means for separating including optical configuration means for performing said separation having symmetry about a center focus.

2. The apparatus of claim 1, wherein said means for separating said reflected light optical configuration having center symmetry is formed by an even numbered plurality of at least four sections, half of said sections comprising optical components for the collection of said diffusely reflected light.

3. In apparatus for measuring diffuse reflectance from an illuminated sample including a source for providing an illuminating radiation beam, means for directing the beam to illuminate a test sample, a reflectance beam detector, and means for directing reflectance from the sample to the detector, the improvement comprising:
   (a) a specular control device having at least a first beam incident surface;
   (b) said first surface divided into an even numbered plurality of at least four sections, half of said sections comprising open beam-passing sections and half of said sections comprising beam-reflecting sections; and
   (c) each of said open sections positioned between a pair of said reflecting sections and opposite one of said open sections, and each of said reflecting sections positioned between a pair of said open sections and opposite one of said reflecting sections.

4. The improvement of claim 3 in which the total surface area of said open sections is equal to the total surface area of said reflecting sections.

5. The improvement of claim 3 in which the total surface area of said open sections is unequal to the total surface area of said reflecting sections.

6. The improvement of claim 3, 4 or 5 including an opaque border space positioned between adjacent pairs of said plurality of sections.

7. The improvement of claim 3 including:
   (a) said specular control device having a second beam incident surface opposite said first beam incident surface;
   (b) said second surface divided into an even numbered plurality of at least four sections, half of said sections comprising open beam-passing sections and half of said sections comprising beam-reflecting sections; and
   (c) said second surface open sections positioned directly opposite said first surface open sections, and said second surface reflecting sections positioned directly opposite said first surface reflecting sections.

8. The improvement of claim 7 in which the total surface area of said second surface open sections is equal to the total surface area of said second surface reflecting sections.

9. The improvement of claim 7 in which the total surface area of said second surface open sections is unequal to the total surface area of said second surface reflecting sections.

10. The improvement of claim 7, 8 or 9 including an opaque border space positioned between adjacent pairs of said second surface plurality of sections.

11. In an apparatus for measuring diffuse reflectance from an illuminated sample including a source for providing an illuminating radiation beam, means for directing the beam to illuminate a test sample, and a reflectance beam detector, the improvement comprising:
   (a) a specular control device having at least a first beam incident surface;
   (b) said first surface divided into a plurality of sections, half of said sections comprising open beam-passing sections and half of said sections comprising beam-reflecting sections; and
   (c) an opaque border space separating adjacent sections of said first surface.

12. The improvement of claim 11 in which the total surface area of said open sections is equal to the total surface area of said reflecting sections.

13. The improvement of claim 11 in which the total surface area of said open sections is unequal to the total surface area of said reflecting sections.

14. The improvement of claim 11, 12 or 13 in which:
   (a) said plurality of sections comprises more than two sections, half of said sections being said open sections and half of said sections being said reflecting sections;
   (b) each of said open sections being positioned between a pair of said reflecting sections and opposite one of said open sections; and
   (c) each of said reflecting sections being positioned between a pair of said open sections and opposite one of said reflecting sections.

* * * * *